(12) United States Patent
Peterson (10) Patent No.: US 8,741,268 B2
(45) Date of Patent: Jun. 3, 2014

(54) DENTAL PROPHYLACTIC PASTE

(75) Inventor: Kenneth S. Peterson, Charlotte, NC (US)

(73) Assignee: Preventive Technologies, Inc., Indian Trail, NC (US)

( * ) Notice: Subject to any disclaimer, the term of this patent is extended or adjusted under 35 U.S.C. 154(b) by 770 days.

(21) Appl. No.: 12/556,913

(22) Filed: Sep. 10, 2009

(65) Prior Publication Data

US 2011/0059420 A1  Mar. 10, 2011

(51) Int. Cl.
*A61K 8/00* (2006.01)
*A61K 8/18* (2006.01)
*A61Q 11/00* (2006.01)

(52) U.S. Cl.
CPC .. *A61K 8/18* (2013.01); *A61Q 11/00* (2013.01)
USPC .......................................................... 424/49

(58) Field of Classification Search
CPC .................................. A61K 8/18; A61Q 11/00
USPC ............... 424/49, 48, 54, 440, 667, 678, 682, 424/719, 78.1, 488, 489, 486, 52, 50, 51, 424/53, 55, 56, 57, 58, 43, 45, 602, 305, 424/309, 401; 433/217.1, 228.1, 199.1, 433/215, 222.1, 32, 2, 216; 523/116, 117, 523/118; 106/35; 423/308
See application file for complete search history.

(56) References Cited

U.S. PATENT DOCUMENTS

| | | |
|---|---|---|
| 3,228,845 A | 1/1966 | Naijar |
| 4,165,366 A | 8/1979 | Mellberg |
| 4,397,837 A | 8/1983 | Raaf et al. |
| 5,037,639 A | 8/1991 | Tung |
| 5,266,304 A | 11/1993 | Baffelli et al. |
| 5,268,167 A | 12/1993 | Tung |
| 5,427,768 A | 6/1995 | Tung |
| 5,437,857 A | 8/1995 | Tung |
| 5,460,803 A | 10/1995 | Tung |
| 5,522,893 A | 6/1996 | Chow et al. |
| 5,534,244 A | 7/1996 | Tung |
| 5,542,973 A | 8/1996 | Chow et al. |
| 5,545,254 A | 8/1996 | Chow et al. |
| 5,562,895 A | 10/1996 | Tung |
| 5,571,502 A | 11/1996 | Winston et al. |
| 5,603,922 A | 2/1997 | Winston et al. |
| 5,605,675 A | 2/1997 | Usen et al. |
| 5,605,677 A | 2/1997 | Schumann et al. |
| 5,614,175 A | 3/1997 | Winston et al. |

(Continued)

OTHER PUBLICATIONS

Chow et al., "The Dynamics of De- and Remineralization," *Journal of Professional Excellence Dimensions of Dental Hygiene*, Feb. 2009.

*Primary Examiner* — Benjamin Packard
(74) *Attorney, Agent, or Firm* — Alston & Bird, LLP (57) ABSTRACT

A dental prophylactic paste having excellent flowability during the manufacturing process, minimal to no splattering during use, and remineralization characteristics is provided. The prophylactic paste includes at least one water soluble calcium salt; a water soluble phosphate salt, a water soluble silicate; and a moisture retention agent. The paste has a splatter rating of less than 3. The splatter rating of the paste refers to the tendency of the paste to splatter during a dental cleaning procedure. The lower the splatter rating, the less the paste has a tendency to splatter. A paste having a splatter rating of less than 3 is considered to have good handability.

22 Claims, 5 Drawing Sheets

(56) References Cited

U.S. PATENT DOCUMENTS

| | | |
|---|---|---|
| 5,645,853 A | 7/1997 | Winston et al. |
| 5,713,738 A * | 2/1998 | Yarborough .................. 433/215 |
| 5,762,911 A | 6/1998 | Kleinberg et al. |
| 5,817,296 A | 10/1998 | Winston et al. |
| 5,833,954 A | 11/1998 | Chow et al. |
| 5,833,957 A | 11/1998 | Winston et al. |
| 5,858,333 A | 1/1999 | Winston et al. |
| 5,866,102 A | 2/1999 | Winston et al. |
| 5,895,641 A | 4/1999 | Usen et al. |
| 5,958,380 A | 9/1999 | Winston et al. |
| 5,976,507 A | 11/1999 | Wong et al. |
| 5,993,786 A | 11/1999 | Chow et al. |
| 6,010,684 A | 1/2000 | Wiedemann |
| 6,036,944 A | 3/2000 | Winston et al. |
| 6,056,930 A | 5/2000 | Tung |
| 6,120,754 A | 9/2000 | Lee et al. |
| 6,159,448 A | 12/2000 | Winston et al. |
| 6,159,449 A | 12/2000 | Winston et al. |
| 6,207,139 B1 | 3/2001 | Lee et al. |
| 6,214,321 B1 | 4/2001 | Lee et al. |
| 6,217,851 B1 | 4/2001 | Kleinberg et al. |
| 6,280,707 B1 | 8/2001 | Peterson et al. |
| 6,303,104 B1 | 10/2001 | Winston et al. |
| 6,372,198 B1 | 4/2002 | Abbate |
| 6,413,498 B1 | 7/2002 | Malmagro |
| 6,440,394 B2 | 8/2002 | Barth et al. |
| 6,451,290 B2 | 9/2002 | Winston et al. |
| 6,482,395 B1 | 11/2002 | Barth et al. |
| 6,485,708 B1 | 11/2002 | Winston et al. |
| 6,497,858 B1 | 12/2002 | Takatsuka et al. |
| 6,521,215 B2 | 2/2003 | Okay |
| 6,793,725 B2 | 9/2004 | Chow et al. |
| 7,182,937 B2 | 2/2007 | Xu et al. |
| 7,387,774 B2 | 6/2008 | Faller et al. |
| 7,619,016 B2 | 11/2009 | Dickens et al. |
| 2002/0137728 A1 * | 9/2002 | Montgomery .................. 514/99 |
| 2004/0047814 A1 | 3/2004 | Xu et al. |
| 2004/0208835 A1 | 10/2004 | Driessens et al. |
| 2005/0084461 A1 | 4/2005 | Winston et al. |
| 2005/0089481 A1 | 4/2005 | Yamanaka et al. |
| 2005/0281759 A1 | 12/2005 | Tung |
| 2006/0110340 A1 | 5/2006 | Tung |
| 2006/0134019 A1 | 6/2006 | Oshino et al. |
| 2006/0171903 A1 | 8/2006 | Yamagishi et al. |
| 2006/0280694 A1 | 12/2006 | Peldyak et al. |
| 2006/0292090 A1 | 12/2006 | Sharma et al. |
| 2006/0292092 A1 | 12/2006 | Sharma et al. |
| 2007/0128131 A1 | 6/2007 | Tokunaga et al. |
| 2007/0183984 A1 | 8/2007 | Haas et al. |
| 2007/0218017 A1 | 9/2007 | Busch et al. |
| 2008/0050407 A1 | 2/2008 | Haas |
| 2008/0193557 A1 | 8/2008 | Reynolds |
| 2008/0226566 A1 | 9/2008 | Poth et al. |
| 2008/0280260 A1 | 11/2008 | Belikov et al. |
| 2008/0292565 A1 | 11/2008 | Tung |
| 2009/0022672 A1 | 1/2009 | Reynolds |
| 2009/0208909 A1 | 8/2009 | Rusin et al. |
| 2009/0305194 A1 | 12/2009 | Rusin et al. |

\* cited by examiner

DENTAL PROPHYLACTIC PASTE

FIELD OF THE INVENTION

The present invention relates to dental prophylactic pastes, and in particular to a dental prophylactic paste having remineralization properties and excellent handability.

BACKGROUND OF THE INVENTION

The American Dental Association recommends regular visits to a dentist for professional cleanings and oral exams in order to help prevent tooth decay and cavities. In a typical professional cleaning, a dental angle with a rotating applicator tip is used to apply dental prophylaxis paste (also referred to herein as prophy paste) to the patient's teeth and scrub any accumulated plaque, tartar and stain off the teeth. The applicator tip typically includes a flexible rubber or latex cup for receiving the prophy paste.

Prophy paste is typically packaged in a small, single-use container. During the cleaning process, a dental professional, such as a dental hygienist, inserts the applicator tip into the container. Typically, the applicator tip is rotated at relatively high speeds, such as between 1,000 and 3500 rpm, to help assist in loading the prophy paste into the cup. Desirably, an appropriate amount of the prophy paste is loaded quickly by the rotating cup so that the dental professional can perform this step in a one-step stab-like action of the cup into the paste. In some cases, the consistency of the paste may be too wet or too dry. For example, if the prophy paste is too wet it may not adequately load fill the cup. On the other hand, if it is too dry or too tacky it may be difficult to load the paste into the cup due in part to the flexibility of the cup. Additional issues related to the consistency of paste may also lead to other problems that are frequently associated with prophy paste. In particular, splattering of the prophy paste during use is of special concern. For example, many commercially available prophy pastes have a tendency to splatter during the actual teeth cleaning process or during the step of picking up the prophy paste with the applicator tip. Again, the consistency of the paste also contributes to the splattering of the paste. Pastes that are too wet or tacky tend to splatter excessively during use. Prophy pastes that have little, if any, splattering and can be picked up relatively easily by the applicator tip are generally referred to as having good handability.

Other handability issues relate to the ease to which the paste can be packaged during the manufacturing process. Typically, prophy pastes are either introduced into the individual containers through extrusion or by a gravity fed system. In the case of the gravity fed system, it is essential that the prophy paste initially be flowable so that it can flow into and fill the individual containers. However, after being introduced into the container, the prophy paste needs to cure or set so that the paste has the desired consistency for use by the end user, such as a dental hygienist. For instance, some prophy pastes are formulated to initially go from a semi-fluid state in which the paste has flowability to a final cured state. If the paste is too thick or tacky, it may create difficulties in filling the containers. On the other hand, if the paste is too wet, it may not cure to the right consistency. Other prophy pastes may be formulated such that little or no additional curing takes place. These types of prophy pastes typically have little flowability and are generally injected under pressure, such as extrusion, into the containers. In many cases, such pastes may be too thick or tacky and, as a result, may have a tendency to splatter or be difficult to load into the cup.

Dental enamel is composed of a crystalline latticework composed of various minerals, the principle component of which is a complex calcium phosphate mineral called hydroxyapatite. Normally, hydroxyapatite is insoluble at normal oral pH levels. However, the consumption of acidic beverages and food lowers the pH within the mouth. Additionally, acids are produced within the mouth by bacteria in plaque biofilm. At these lower pH levels the solubility of hydroxyapatite increases, which can lead to demineralization of dental enamel. Demineralization can result in the formation of voids, such as carious lesions, in the teeth that can lead to weakening and loss of enamel.

Recently, dental products have been developed that have remineralization properties. Remineralization refers generally to the process of restoring minerals in the form of mineral ions, such as calcium and phosphate ions, to dental enamel that have been lost due to demineralization. However, currently available prophy pastes that claim to have remineralization properties have a tendency to be difficult to load into the applicator tip cup and also have undesirable levels of splattering. As such, these prophy pastes have generally been considered to exhibit poor handability. As a result, the commercial acceptance of such remineralization prophy pastes has been limited.

Thus, there exists a need for a dental prophy paste having remineralization characteristics without sacrificing the handability (e.g., flowability, low splatter, etc.) of the paste.

BRIEF SUMMARY OF THE INVENTION

The present invention is directed to a dental prophylactic paste that overcomes many of the above-described problems. In particular, embodiments of the present invention provide a prophy paste having excellent flowability during the manufacturing process, minimal to no splattering during use, and remineralization characteristics.

In one embodiment, the present invention provides a dental prophylactic paste having comprising at least one water soluble calcium salt; a water soluble phosphate salt, a water soluble silicate; and a moisture retention agent, wherein the paste has a splatter rating of less than 3. As explained more fully below, the splatter rating of the paste refers to the tendency of the paste to splatter during a dental cleaning procedure. The lower the splatter rating, the less the paste has a tendency to splatter. In the context of the present invention, a paste having a splatter rating of less than 3 is considered to have good handability.

Further, prophy pastes in accordance with the invention provide for remineralization of carious lesions that have been treated with the prophy paste. In this regard, scanning electron micrograph (SEM) images of dentin disk treated with the inventive prophy paste shows that substantially all of the treated areas of the dentin disk treated have been remineralized.

The inventors of the present invention have discovered that remineralization properties can be achieved while providing improved handability by controlling the ratio of the moisture retention agent, water, and silicate matrix to the total amount of calcium and phosphate salts and when present, fluoride containing compounds. In particular, it is desirable that the silicate matrix and a total amount of the calcium and phosphate in the paste be present in a ratio that ranges from about 0.25:1 to 0.75:1. In a preferred embodiment, the amount of sodium silicate and methyl salicylate and a total amount of the calcium and phosphate salts and fluoride containing compounds in the prophy paste are present in a ratio ranging from about 0.15 to 0.3:1.

Further, it is also desirable for the moisture retention agent and a total amount of the calcium and phosphate salts in the paste be present in a ratio ranging from about 1.5:1 to 5.5:1. In a preferred embodiment, the ratio of the silicate matrix to the total amount of the calcium and phosphate in the paste is about 0.3:1. In one embodiment, the water and a total amount of the calcium and phosphate salts in the paste are present in a ratio from about 0.4:1. In further embodiments, the amount water and a total amount of the calcium and phosphate salts and fluoride containing compound in the prophy paste are present in a ratio ranging from about 0.1:1 to 0.3:1, with a ratio of about 0.2:1 being somewhat more preferred.

The prophy may also include abrasive agents. Suitable abrasive agents include amorphous aluminum silicate, also commonly known as pumice, fused sodium potassium aluminum silicate, also commonly know as perilite, diatomaceous earth, and combinations thereof. When present, the amount of abrasive agent generally ranges from about 24 to 48 weight percent, based on the total weight of the prophy paste, and in particular from about 26 to 44 weight percent, and more particularly from about 28 to 42 weight percent. Preferably, the ratio of abrasive agent to the total amount of calcium and phosphate salts and fluoride in the paste ranges from about 1.5:1 to 3.5:1, with a ratio ranging from about 1.5:1 to 3:1 being somewhat more preferred, and a ratio of 2:1 to 3:1, being even more preferred.

In one embodiment, the present invention provides a dental prophylactic paste having low splattering and remineralization properties comprising from about 3 to 6 weight percent of a phosphate salt, from about 2 to 12 weight percent of a calcium salt; from about 0.02 to 12 weight percent of a fluoride containing compound, from about 1 to 8 weight percent of a combination of an alkali silicate and a salicylate, from about 0.02 to 2 weight percent of sodium carboxymethyl cellulose, from about 36 to 42 weight percent glycerin, from about 2 to 6 percent water, and from about 24 to 48 weight percent of an abrasive agent.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

The present invention is directed to a dental prophylactic paste that helps to effect remineralization of dental enamel without sacrificing the desired handability characteristics of the paste. In particular, the inventive prophy pastes include a source of calcium and phosphate ions that are capable remineralizing regions of the tooth enamel where demineralization has occurred. In addition, prophy pastes in accordance with the present invention also exhibit good handability characteristics during the manufacturing process as well as during the dental cleaning process. As discussed in greater detail below, prophy pastes in accordance with the present invention among other things exhibit minimal to no splattering as well as excellent pick-up by the cup of the applicator tip.

Prophy pastes in accordance with the present invention comprise a silicate matrix, water, a moisture retention agent, at least one water-soluble calcium containing compound, and at least one water-soluble phosphate containing compound. In some embodiments, the prophy paste may also include at least one water-soluble fluoride containing compound.

Figure 1:
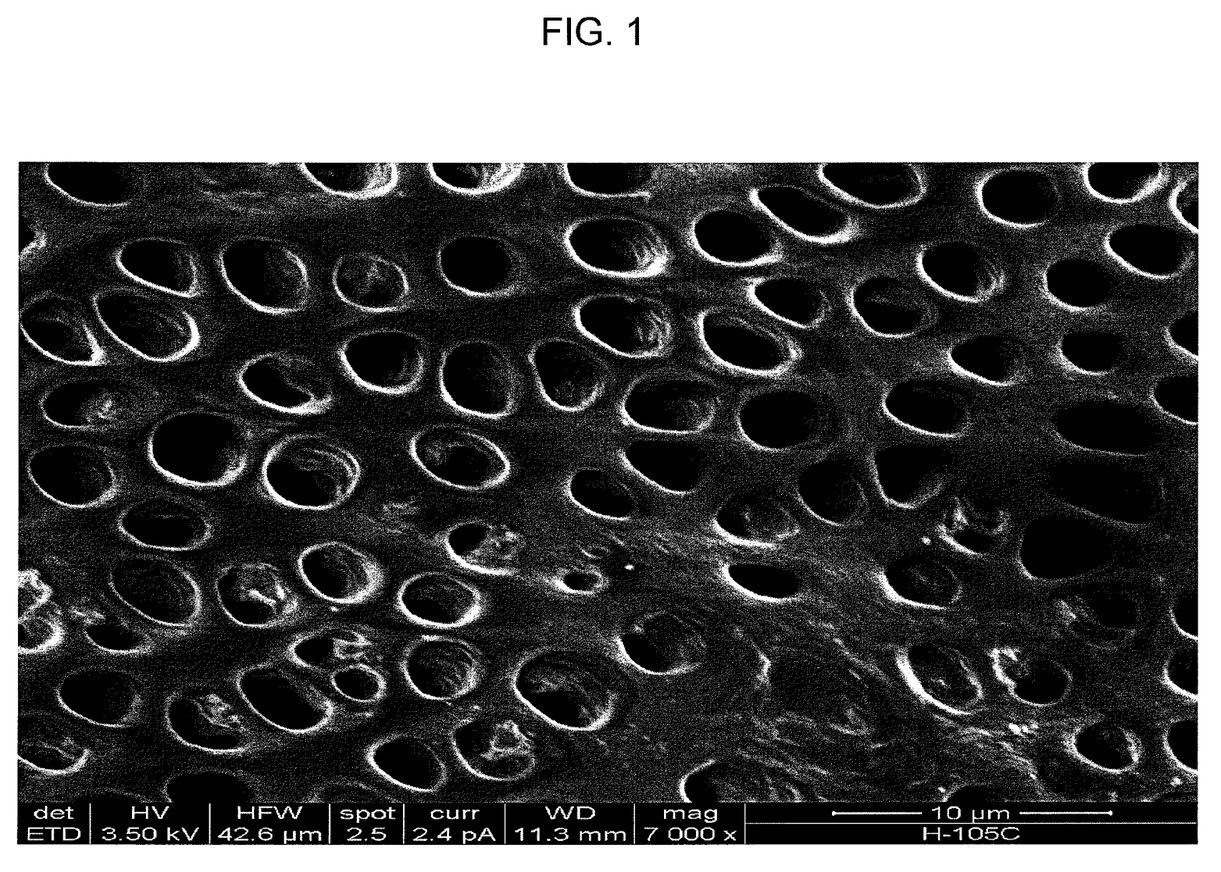
FIG. 1 is an Scanning Electron Microscope (SEM) image of a demineralized dentin disk having open dental canaliculi that has not been treated with the inventive prophy paste.
Figure 2:
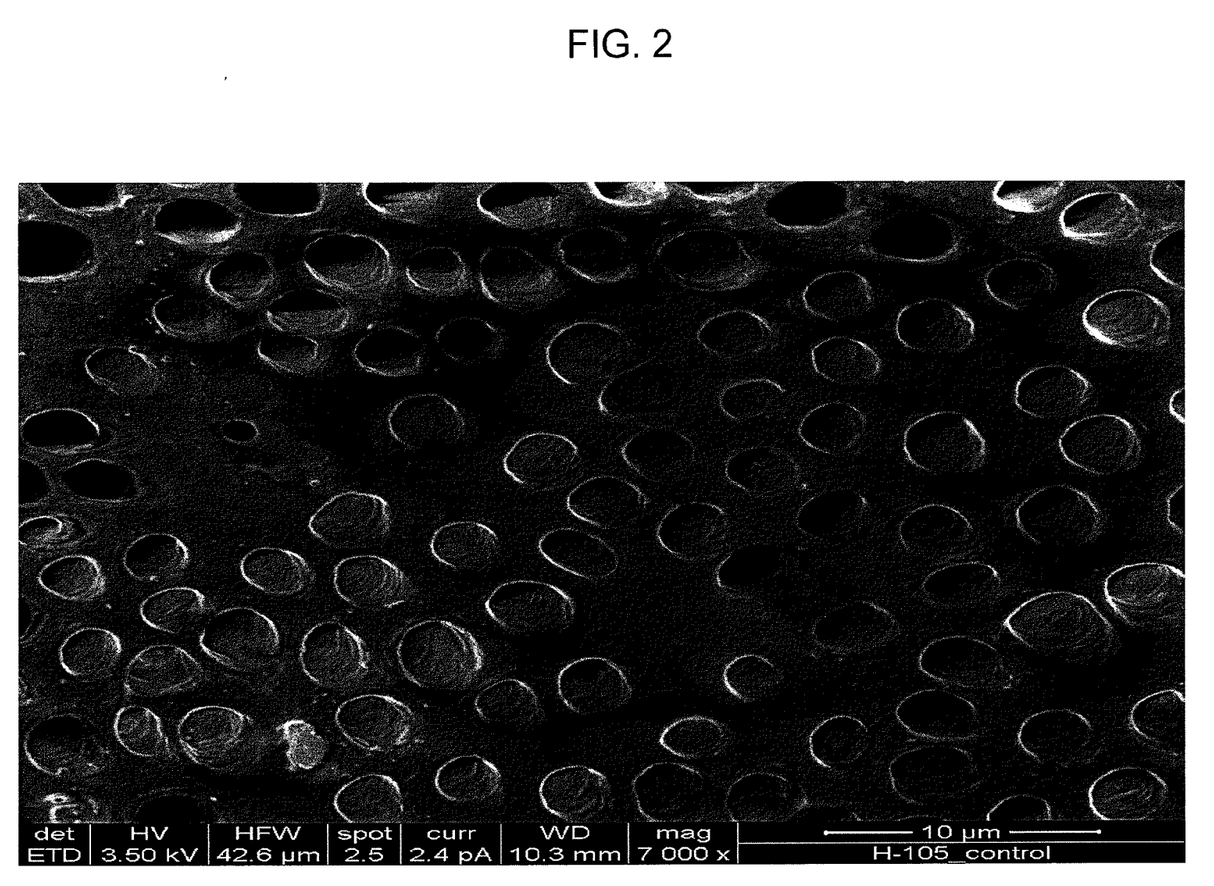
FIG. 2 is an SEM image of a demineralized dentin disk having open dental canaliculi that has been treated with water only.
Figure 3:
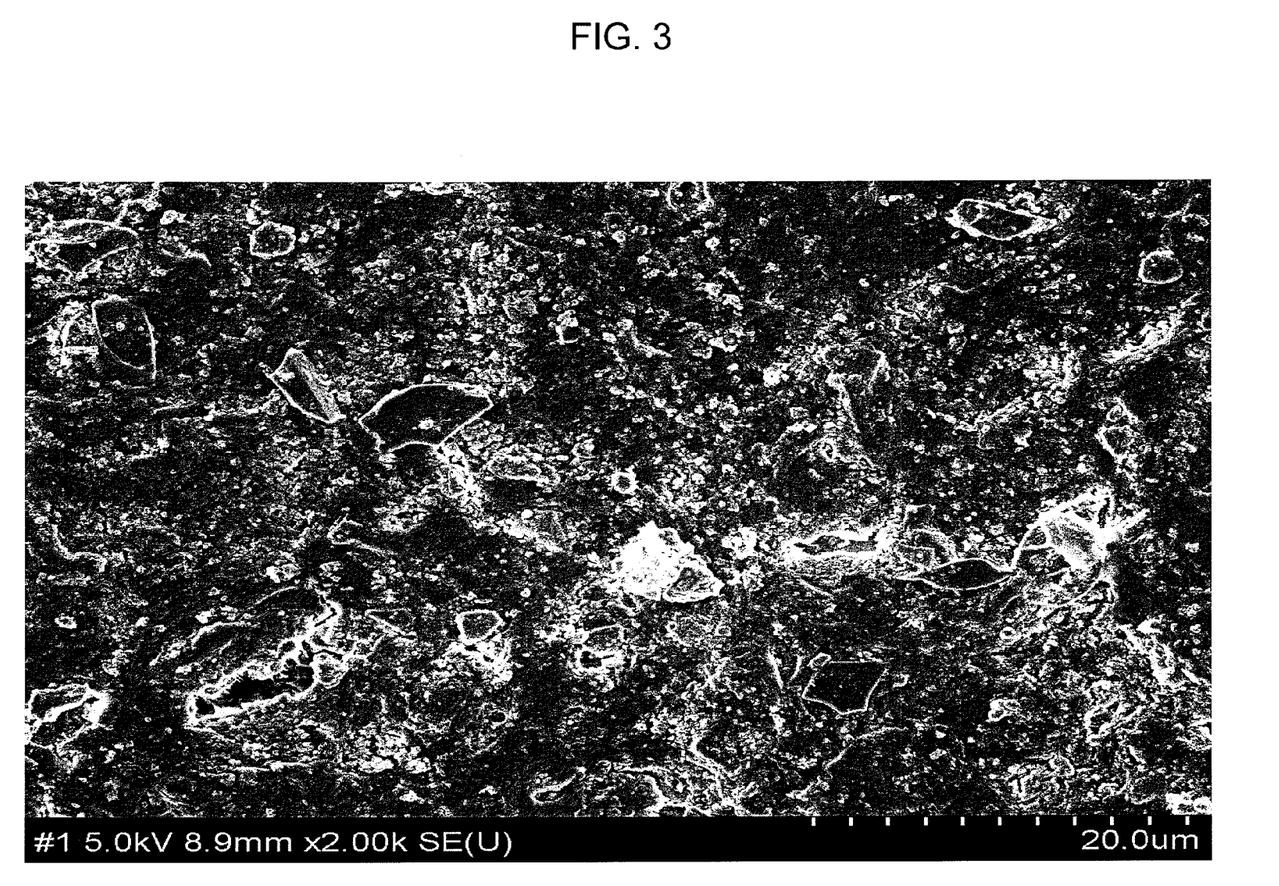
FIGS. 3 and 4 are SEM images of demineralized dentin disk having open dental canaliculi that have been treated with embodiments of the inventive prophy paste.
Figure 4:
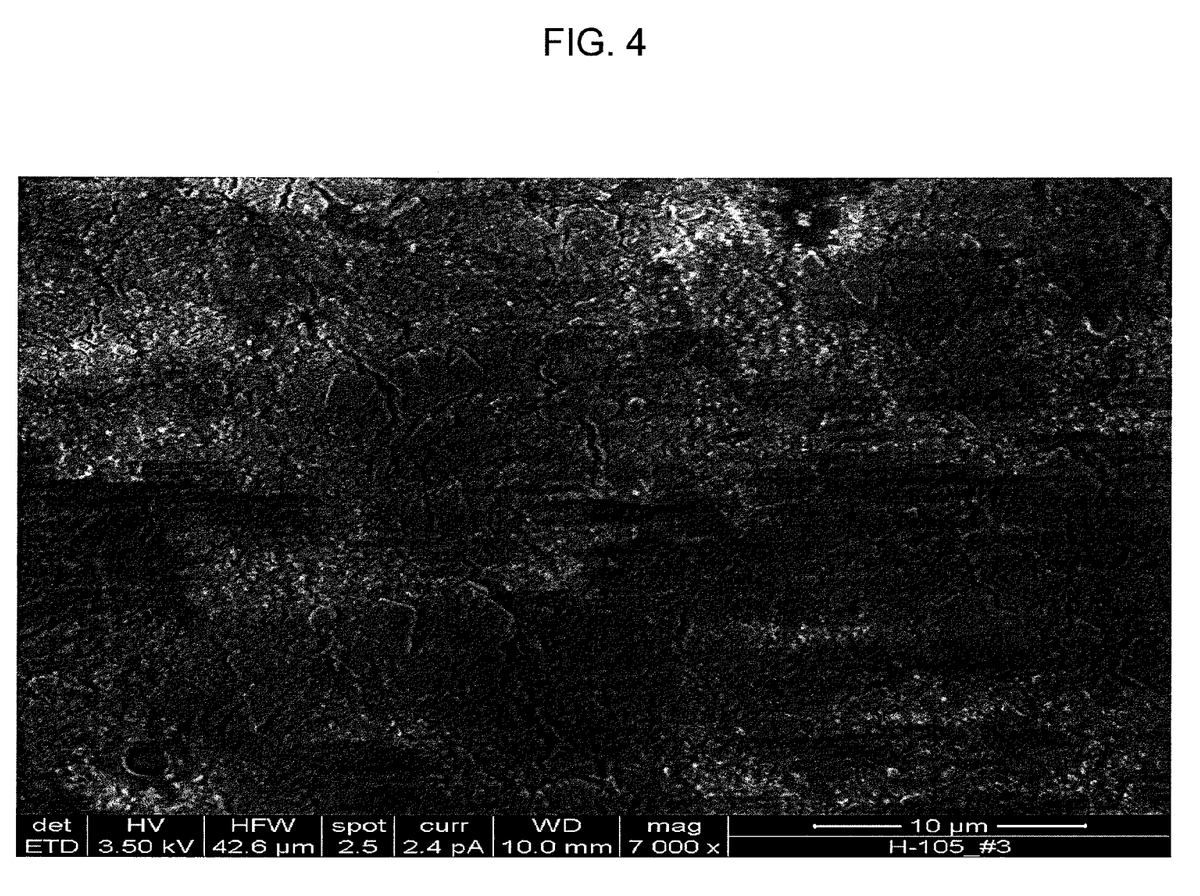

The water-soluble inorganic calcium, phosphate, and when present, fluoride compounds, effect remineralization of dental enamel during the dental cleaning process. As discussed above, demineralization due to acids in the mouth can lead to the presence of carious legions in the dental enamel. In the present invention, the prophy paste provides calcium and phosphate ions that penetrate into the void spaces in the teeth created by demineralization to fill the spaces. In this regard, FIGS. 1-4 are SEM images of dental enamel that show the remineralization characteristics of the inventive prophy paste. In FIG. 1, an SEM image of a dentin disk that has not been treated with a remineralization prophy paste is shown. It can be clearly seen that the dentin disk has numerous open dental canaliculi that are a result of demineralization of the tooth surface. In FIG. 2, an SEM image of a control dentin disk is provided. Here, the dentin disk was treated only with water. The dentin disk retains numerous open dental canaliculi that can be seen on the surface of the demineralized tooth. FIGS. 3 and 4 are SEM images of dentin disks that have been treated with a prophy paste comprising calcium, phosphate and fluoride containing compounds that is in accordance with the present invention. In the images it can be seen that the void spaces or open dental canaliculi visible on the tooth surface have been substantially remineralized. In particular, at least 90% and up to 95-99.9% of the open dental canaliculi have been filled after treatment with the prophy paste. FIGS. 1-4 are discussed in greater detail below in the EXAMPLE SECTION.

While not wishing to be bound by theory, it believed that the calcium, phosphate, and fluoride ions diffuse through the tooth surface to remineralize the demineralized tooth enamel. In one embodiment, the prophy paste is applied to a patient's tooth enamel using a rapidly rotating rubber cup or cup brush during a routine dental professional cleaning. While the length of contact time between the paste and tooth surface is not critical, it is desirable for the time to be great enough to allow the calcium, phosphate, and when present, fluoride ions, to remineralize the demineralized portions of the tooth. Generally, it is desirable for the prophy paste to remain in contact with the tooth surface for at least 10 seconds prior rinsing.

Suitable water-soluble calcium compounds include calcium chloride, calcium bromide, calcium nitrate, calcium acetate, calcium gluconate, calcium benzoate, calcium glycerophosphate, calcium formate, calcium fumarate, calcium lactate, calcium butyrate and calcium isobutyrate, calcium malate, calcium maleate, calcium propionate, calcium valerate or mixtures of water-soluble calcium compounds. In a preferred embodiment, the water-soluble calcium compound comprises calcium malate. Typically, the concentration of the water-soluble calcium compound in the prophy paste is from about 1 to 15 weight percent, based on the total weight of the composition, and in particular, from about 2 to 12 weight percent. In a preferred embodiment, the amount of the water-soluble calcium compound is from about 6 to 10 weight percent.

Suitable water-soluble inorganic phosphates within the scope of the present invention are, for example, alkali salts and ammonium salts of orthophosphoric acid, such as potassium, sodium or ammonium orthophosphate, monopotassium phosphate, dipotassium phosphate, tripotassium phosphate, monosodium phosphate, disodium phosphate and trisodium phosphate and tricalcium phosphate. In a preferred embodiment, the water-soluble phosphate compound comprises disodium hydrogen phosphate or tricalcium phosphate. Typically, the concentration of the water-soluble phosphate compound in the prophy paste is from about 1 to 15 weight percent, based on the total weight of the composition, and in particular, from about 2 to 12 weight percent. In a preferred embodiment, the amount of the water-soluble phosphate compound is from about 3 to 8 weight percent.

As noted above, the inventive prophy pastes may also include fluorine containing compounds. It is believed that the use of a fluoride ions in addition to the calcium and phosphate ions helps the remineralized enamel to be even more resistant to demineralization than the original enamel. Suitable fluoride containing compounds include alkali fluorides such as sodium, potassium, lithium or ammonium fluoride, tin fluoride, indium fluoride, zirconium fluoride, copper fluoride, nickel fluoride, palladium fluoride, fluorozirconates such as sodium, potassium or ammonium fluorozirconate or tin fluorozirconate, fluorosilicates, fluoroborates, fluorostannites. Preferred fluoride containing compounds are sodium fluoride, sodium monfluorophophate, or mixtures thereof. In some embodiments, the prophy paste may also include organic fluorides, such as the known amine fluorides. Fluoride containing compounds may be present in amounts ranging from about 0.02 to 12.0 weight percent, based on the total weight of the composition, and preferably from about 0.02 to 10.0 weight percent.

In order to effect remineralization of the dental enamel, an effective amount of the desired cations and anions must be employed in the oral cavity. Preferably, the concentration of the calcium ions in the mouth during application of the prophy paste is at least about 2 milligram/gram, and more preferably more than about 15 milligrams/grams. Preferably, the concentration of the phosphate ions in the mouth during application of the prophy paste is at least about 2 milligram/gram, and more preferably more than about 5 milligrams/grams. Preferably, the concentration of the fluoride ions in the mouth during application of the prophy paste is at least about 2 milligram/gram, and more preferably more than about 10 milligrams/grams.

In addition to the remineralization properties discussed above, prophy pastes in accordance with the present invention also exhibits excellent handability in relation to the manufacturing process as well as use by the end user. In particular, the prophy paste demonstrates little to no splattering during the step of loading the paste into the cup of the applicator tip as well as when the paste is applied to the teeth of the dental patient.

The desirable handability properties of the inventive prophy pastes are due in part to the combination of the silicate matrix, water, and moisture retention agent. Further, it has been discovered that by selecting the appropriate ratio of the remineralization components (e.g., calcium, phosphate, fluoride) to the silicate matrix components, moisture retention agent, and water, prophy pastes having remineralization properties as well as improved handability can be achieved. Further the desirable handability/splatter control properties are achieved within the scope of the inventive prophy paste when the combination ratios of remineralization components to silicate matrix is about 3 to about 5.5 to 1, remineralization components to moisture retention agents is about 0.4 to about 0.6 to 1 and remineralization components to water is about 3 to about 13 to 1 with the ratio of 6 to about 10 to 1 being preferred.

As noted above, the combination of the silicate matrix, water, and moisture retention agent help control and provide the desirable handling characteristics of the paste during manufacturing and packaging as well as helping to reduce spattering and improve ease of use by the end user, such as the dental hygienist. As alluded to previously, handability of the paste refers generally to the desirable properties of having initial flowability and self leveling attributes during the manufacturing and packaging as well as the low splattering and ease of loading the paste into an applicator tip cup. At the manufacturing and packaging side of the process, the inventive prophy paste has an initial flowability that allows the paste to be gravity fed or easily pumped under relatively low pressure into the individual prophy paste containers. After being introduced into the individual containers, the prophy paste continues to cure to a final and desired consistency. In a preferred embodiment, the prophy paste quickly self levels to an enhanced appearance and continues to cure to a final and desired consistency without any external heating or cooling.

At the end user side of the process, for example, at the dentist office, the prophy paste has a desired consistency such that storage orientation of the individual containers is not critical and the prophy paste does not thin out or become tacky when used with a rapidly rotating applicator tip and there is little to no splattering during use or loading of the applicator tip. Further, in embodiments of the present invention, the prophy paste can typically be loaded by the dental hygienist in a simple one-step process in which the applicator tip cup is inserted into the paste container while rotating. Desirably, prophy pastes in accordance with the present invention have a splatter rating of less than 3, and more desirably less than 2. As explained more fully in the EXAMPLE SECTION below, the splatter rating of the prophy paste refers to the tendency of the prophy paste to collect or adhere to the exterior surface of the applicator tip cup. The tendency of the paste to adhere to the exterior surface of the applicator tip cup is indicative of the paste's likelihood to splatter during use, either when loading or when applied to the teeth of a patient. Under the splatter test rating, a higher number correlates to a stronger tendency to splatter. Prophy pastes with little to no splatter are generally classified as having a splatter rating that is between 1 and 3. Prophy pastes having a splatter rating above 4 are not considered to be acceptable as the amount of splatter is too high.

The silicate matrix of the prophy paste includes a combination of a water-soluble silicate, such as an alkali metal silicate, and a salicylate or an acid forming agent. Generally, the curing system is present in the prophy paste in an amount that ranges from about 1 to 10 weight percent, based on the total weight of the composition, and in particular from about 2 to 8 weight percent.

Alkali metal silicates that can be used in the present invention includes sodium silicate and potassium silicate, and combinations thereof. The alkali metal silicate is typically present in an amount ranging from about 2 to 10 weight percent, based on the total weight of the composition, and in particular, from about 3 to 6 weight percent.

Salicylates that can be used in accordance with the present invention include methyl salicylate, also commonly known as sweet birch oil or oil of wintergreen. Salicylates when used as part of the silicate matrix system can be present in the paste at a concentration from about 0.2-2.5 weight percent, with a concentration between 0.5 and 1.5 weight percent being preferred. Additional methyl salicylate of up to 1.0 weight percent may be added as the flavor agent Wintergreen. In a preferred embodiment, the amount of salicylate is about 0.8 to 1.2 weight percent. Acid forming agents that may be used in accordance with the present invention include anhydrides, such as succinic, acetic, maleic or fumaric anhydride, or amides such as acetamide or esters such as glyceryl diacetate, or glyceryl triacetate also known as triacetin. Acid forming agents can be present in amounts from about 0.2 to 2 weight percent, based on the total weight of the composition. In a preferred embodiment, the amount of acid forming agent is from about 0.5 and 1.0 weight percent.

In a preferred embodiment, the silicate matrix comprises a combination of sodium silicate, methyl salicylate and sodium carboxymethycellulose. In this embodiment, the sodium silicate and methyl salicylate together form the silicate matrix of the composition in the ratios of sodium silicate 2.0 to 6.0 to methyl salicylate 0.1 to 1.2 parts.

The moisture retention agent, also referred to as a humectant, contribute to the handling characteristics of the prophy paste including moisture control, flavor solvent, flavor retention, and rinseability. Suitable moisture retention agents that may be used in accordance with the present invention include glycerin, sorbitol, propylene glycol, polyethylene glycols, and other non-toxic glycols, and mixtures thereof. Glycerin is a preferred moisture retention agent.

The amount of the moisture retention agent in the prophy paste typically ranges from about 10 to 60 weight percent, based on the total weight of the paste, with an amount ranging from about 20 to 50 weight percent being more preferred. In a particularly preferred embodiment, the amount of the moisture retention agent is from about 30 to 45 weight percent, with about 33 to 42 weight percent being more preferred. It should be understood that the exact amount of the moisture retention agent can be varied within reasonable limits without significantly altering the initial flowability and self leveling of the prophy paste prior to curing/setting, or significantly altering the handling and non splattering characteristics of the prophy paste.

The water can be present as free water, water of hydration, or a mixture thereof. Water is typically present in the prophy paste in an amount that is from about 1 to 10 weight percent based on the total weight of the composition, and in particular from about 2 to 8 weight percent.

The prophy paste may also include various abrasive agents that assist in the removal of stains, tartar and polishing of the enamel surface. Suitable abrasive agents include amorphous aluminum silicate, also commonly known as pumice powder, fused sodium potassium aluminum silicate, also commonly know as perilite, diatomaceous earth, and combinations thereof. When present, the amount of abrasive agent generally ranges from about 24 to 48 weight percent, based on the total weight of the prophy paste, and in particular from about 26 to 44 weight percent, and more particularly from about 28 to 42 weight percent. Typically, prophy pastes in accordance with the present invention can be prepared as fine, medium, or coarse grit compounds, and in particular, as Lower Abrasion, Medium Abrasion, or Higher Abrasion pastes as specified in ANSI/ADA Specification No. 62 (2005). Preferably, the prophy paste does not exceed the limits for the specified abrasion level as set forth in ANSI/ADA Specification No. 62.

In embodiments having abrasive agents, it has been discovered that improved handability, both flow and curing of the paste during manufacturing, and during the cleaning process by a dental profession can be achieved by having a ratio of abrasive agents to the remineralization components that is from about 6:1, and in particular, from about 4:1. Preferably, the ratio of abrasive agents to the remineralization components in the paste is from about 1.5 to 1 to about 3.5:1.

Additional additives that may be included in the prophy paste include buffering agents, gelling agents, flavorants, sweeteners, colorants, and the like.

Buffering agents that may be used in the present invention include monosodium phosphate, sodium citrate, sodium benzoate, and mixtures thereof. Generally, buffering agents may be present in the prophy paste in an amount from about 0.01-to 0.5 weight percent, based on the total weight of the composition.

Gelling agents that may be used in accordance with the present invention include carboxymethyl cellulose, hydorxymethyl cellulose, hydroxylpropyl cellulose, xanthan, carageenan, and mixtures thereof. Gelling agents are present in the prophy paste in an amount from about 0.01-to 1.0 weight percent, based on the total weight of the composition.

Examples of sweetening agents include sodium saccharin, aspartame, sucralose, xylitol, and mixtures thereof. Typically, the sweetening agent can be present in the prophy paste at levels of about 0.01-0.5 percent by weight. Generally, any known flavoring agents for use in dental hygiene products can be used in the present invention. Flavoring agents are typically present in amount up to about 1 to 2 percent by weight.

Coloring agents include FD&C Blue #1, FD&C Blue #2, FD&C Yellow #10, FD&C Red 40 and combinations thereof. The coloring agents are generally present in the prophy paste at levels of about 0.01-0.1 percent by weight. Coloring agents can also be used to visually identify the abrasion grades of the prophy paste.

Embodiments of the present invention may also include a desensitizing agent. Examples of desensitizing agents include potassium bicarbonate, potassium citrate, potassium chloride, potassium nitrate, strontium chloride, strontium acetate, strontium nitrate, or mixtures thereof.

EXAMPLES

The following examples are provide to illustrate embodiments of the invention and should not be construed as limiting the invention.

Remineralization

In this example, the reminarilization characteristics of embodiments of the inventive prophy paste were explored. Four different dentin disks were prepared from extracted human teeth. The entire surface of the dentin disk was lightly etched with a standard phosphoric acid tooth conditioning gel to remove the smear layer. The etched disks were examined with SEM to ensure that etching was complete. The etched disks were divided into four treatment groups. The first treatment group was treated only with water. The second and third treatment groups were treated with remineralization prophy pastes in accordance with the present invention. The compositions of the second and third groups are described in Tables 1 and 2 below, respectively. The fourth treatment group was treated with Enamel Pro®, Medium Grit. Each treatment was applied to the assigned etched dentin disks using a Pivot® Disposable Prophy Angle with a Non-Latex Soft Cup applicator tip for 10-15 seconds. The treatment was then allowed to remain in place on the dentin disks for 1 minute followed by rinsing with water for 10 seconds. SEM images of each of the disks were then obtained.

TABLE 1

Sample 1: Course Grit

| Ingredient Name | (% w/w) |
|---|---|
| Purified Water | 1.40 |
| Glycerin | 37.00 |
| Calcium Malate | 8.00 |
| Sodium MFP | 9.40 |
| Sodium Phosphate Dibasic | 5.00 |
| Sodium Silicate | 5.00 |
| Methyl Salicylate | 0.80 |
| Pumice 0 | 6.25 |
| Pumice FF | 25.0 |
| Flavorant | 0.90 |
| Sodium Carboxymethyl Cellulose | 0.05 |
| Sodium Saccharin | 0.04 |
| Monosodium Phosphate | 0.16 |
| Red 40 1%/Glycerin | 1.00 |
| Total | 100 |

TABLE 2

Sample 2: Medium Grit

| Ingredient Name | (% w/w) |
|---|---|
| Purified Water | 1.65 |
| Glycerin | 37.00 |
| Calcium Malate | 8.00 |
| Sodium MFP | 9.40 |
| Sodium Phosphate Dibasic | 5.00 |
| Sodium Silicate | 5.00 |
| Methyl Salicylate | 0.80 |
| Pumice FF | 31.00 |
| Flavorant | 0.90 |
| Socium Carboxymethyl Cellulose | 0.05 |
| Sodium Saccharin | 0.04 |
| Monosodium Phosphate | 0.16 |
| Blue #1/Blue #2/Glycerin | 1.00 |
| Total | 100 |

Figure 5:
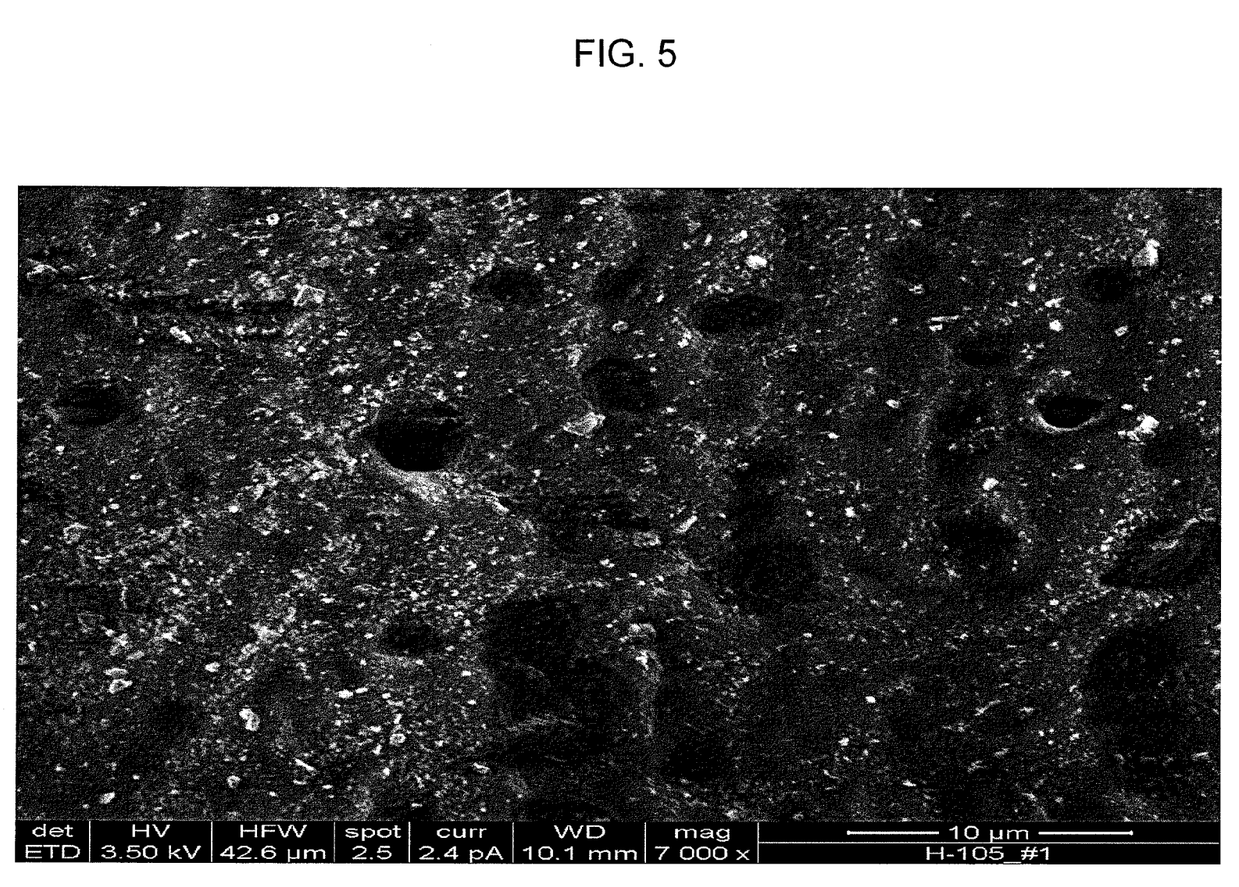
FIG. 5 is an SEM image of a demineralized dentin disk having open dental canaliculi that have been treated with a commercially available remineralization paste sold under the trademark Enamel Pro® available from Premie®.

FIG. 1 is an SEM image of an etched dentin disk prior to treatment. Numerous open dental canaliculi are visible on the surface of the disk. FIG. 2 is an SEM following treatment with water. In FIG. 2 it can be seen that numerous open dental canaliculi are still present following treatment. FIGS. 3 and 4 are SEM images of dentin disks that have been treated with Samples 1 and 2, respectively. From these images, it can clearly be seen that the open dental canaliculi have been filled and reminarilization has occurred. FIG. 5 is an SEM image of a dentin disk that has been treated with a commercial available reminarization paste sold under the trademark Enamel Pro® available from Premie®. While the Enamel Pro® filled and remineralized many of the open dental canaliculi, it can be seen from the SEM image that the filling and remineralization was incomplete and that many open dental canaliculi remained.

Handability

In the following examples the handability, and in particular, the splatter rating of the inventive prophy pastes was explored. Specifically, the handability of the inventive prophy paste was compared to Enamel Pro® prophy paste available from Premier®. In these examples, a rotating applicator tip having a cup was inserted into a prophy paste container. The applicator tip was rotated between 1,500 and 2,000 rpm and the tip was inserted into the cup 10 times with a residence time of about 1 second per insertion. The average percentage of prophy paste material adhering to the outside surface of the cup was then determined. As previously discussed above, the tendency of the prophy paste to adhere to the outside surface of the cup is an indication of whether or not the prophy paste has a tendency to splatter during use.

Equipment Supplies:

The following equipment was used in evaluating the handability of the prophy paste.

NSK Variable Controller: (Speed 1-8, 600-2500 rpm) with handpiece attachment, Model EZ Prohpy Model NE 66;

Disposable Prophylaxis Angle: PIVOT® with flexible, soft non-latex cup (synthetic rubber), Item No. 110004 available from Preventech of Indian Trail, N.C.;

Top Loading Balance:Ohaus Valor 3000, Modely V31XH202 (200 g×0.01 g) and Model V31SH2 (2000 g×0.1 g);

Prophylaxids cup holder adhered to a 6"×6" ceramic tile;

Prophylaxis Paste individually packaged in 2 gram cups;

Distilled Water; and

Microbrush Utrabrush No. 2.

Experimental Procedure:

In the first step, the prophylaxis paste sample to be tested was inserted into a prophylaxis cup holder that was adhered to the ceramic tile. The loaded prophylaxis cup holder and cup of prophylaxis paste were then placed onto the Ohaus Model V31XH2 scale and the scale zero balanced. A Disposable Prophylaxis Angle (DPA) was then fitted onto the EZ Prophy handpiece. The controller was set between speeds 5-6 (1,500-2,000 rpm). One brush stroke of water was applied to the prophy paste and to the inside of cup on the applicator tip of the DPA. The EZ prophy was then turned on so that the DPA was spinning at between approximately 1,500 to 2,000 rpm. The rotating DPA cup was then inserted (plunged) into the prophy paste that was previously placed on the scale. The DPA cup was plunged into the paste for a total of 10 consecutive plunges, with each plunge applying no more than 350 grams on the scale. Each plunge had a residence time of about 1 second. The DPA was then removed and weighed. The DPA cup was also visually inspected for the presence of paste on the exterior of the cup. The weight of the un-loaded DPA is subtracted from the filled DPA to determine the total amount of pasted picked up the DPA applicator cup. From this value, the average weight amount of prophy paste needed to manually fill a DPA applicator cup was subtracted to determine the total excess prophy paste adhered to the outside of the applicator cup. The average weight of prophy paste need to fill an applicator cup was previously determined by manually filling ten applicator tip cups with prophy paste. This test was repeated on both the inventive prophy paste and the Enamel Pro® prophy paste 10 times. The results are summarized below.

Experimental Observations and Results

After testing, the DPA applicator cups loaded with the Enamel Pro® prophy paste had noticeable accumulation of the prophy paste on the exterior sidewalls of the cup. The presence of the residual paste is an indication of the tackiness of the paste, and hence it propensity to splatter during use. In contrast, the applicator cups loaded with the inventive prophy paste had little to no accumulation of paste on the exterior of the DPA applicator cup. From observations made during this testing, it was determined that samples that had an add-on weight of more than 15% to the exterior of the DPA applicator cup also had an unacceptable level of splattering. On the other hand, samples that had less than 15% excess add-on of applicator cup showed minimal to no splattering. Table 3 below summarizes the results.

TABLE 3

Percent Excess Prophy Paste Loading

| Trial No. | Excess Inventive Prophy Paste (g) | % Excess Inventive Prophy Paste | Excess Enamel Pro ® (g) | % Excess Enamel Pro ® |
|---|---|---|---|---|
| Trial 1 | 0.00 | 0.0 | 0.03 | 37.5 |
| Trial 2 | 0.01 | 12.5 | 0.04 | 50 |
| Trial 3 | 0.01 | 12.5 | 0.01 | 12.5 |
| Trial 4 | 0.00 | 0 | 0.02 | 25 |
| Trial 5 | 0.00 | 0 | 0.03 | 37.5 |
| Trial 6 | 0.01 | 12.5 | 0.03 | 37.5 |
| Trial 7 | 0.00 | 0.00 | 0.03 | 37.5 |
| Trial 8 | 0.00 | 0 | 0.02 | 25 |
| Trial 9 | 0.00 | 0 | 0.03 | 37.5 |
| Trial 10 | 0.01 | 12.5 | 0.02 | 25 |
| % Excess Average | — | 5 | — | 32.5 |

A scale for the Handability/Splatter rating of the prophy paste based on the amount of excess prophy paste adhered to the exterior of the DPA applicator cup is provided in Table 4 below. From this experiment, it was determined that a Handability/Splatter rating of less than 3, and preferably less than 2 provided a prophy paste have minimal to no splattering during use and loading of the applicator tip cup.

TABLE 4

Prophy Paste Handability/Splatter Rating

| Splatter rating | % Excess Add-On Prophy Paste |
|---|---|
| 1 | 0-5 |
| 2 | 6-10 |
| 3 | 11-15 |
| 4 | 16-20 |
| 5 | 21-25 |
| 6 | 26-30 |
| 7 | 31-35 |
| 8 | 36-40 |
| 9 | 41-45 |
| 10 | 46-50 |

TABLE 5

SAMPLES 5-15: Prophy Pastes Formulations Having Acceptable Handability/Splatter Rating

| Ingredient | Sample #5 | Sample #6 | Sample #7 | Sample #8 | Sample #9 | Sample #10 | Sample #11 | Sample #12 | Sample #14 | Sample #15 |
|---|---|---|---|---|---|---|---|---|---|---|
| Glycerin | 38.00 | 37.00 | 38.35 | 35.00 | 34.75 | 35.25 | 36.00 | 36.00 | 37.00 | 36.00 |
| Pumice FF | 28.00 | 26.75 | 29.00 | 26.50 | 26.00 | 25.00 | 24.00 | 22.75 | 32.00 | 37.00 |
| Pumice O | 8.00 | 9.00 | 10.00 | 9.50 | 12.00 | 12.00 | 12.00 | 12.00 | 0.00 | 0.00 |
| Sodium Fluoride | 2.75 | n/a | 2.80 | n/a | n/a | n/a | n/a | n/a | n/a | 2.70 |
| Sodium MFP | n/a | 9.40 | n/a | 9.00 | 9.40 | 9.40 | 9.40 | 9.40 | 9.40 | n/a |
| Calcium Citrate | 10.00 | | n/a | n/a | | | n/a | n/a | | |
| Calcium Malate | n/a | 8.00 | 10.00 | 7.50 | 8.00 | 8.00 | 8.00 | 8.00 | 8.00 | 8.00 |
| Calcium Citrate Malate | n/a | n/a | n/a | n/a | n/a | n/a | n/a | n/a | n/a | 2.00 |
| Sodium Phosphate Dibasic | n/a | n/a | n/a | n/a | n/a | n/a | n/a | n/a | 5.00 | n/a |
| Calcium Phosphate Tribasic | n/a | 3.00 | 3.00 | 2.80 | 3.00 | 3.00 | 3.00 | 3.00 | n/a | 3.00 |
| Water | 2.36 | 2.00 | 2.00 | 4.20 | 2.00 | 2.00 | 2.25 | 3.00 | 1.65 | 5.25 |
| Sodium Saccharin | 0.04 | 0.04 | 0.04 | 0.04 | 0.04 | 0.04 | 0.04 | 0.04 | 0.04 | 0.04 |
| Xylitol | n/a | n/a | n/a | n/a | n/a | n/a | n/a | n/a | n/a | n/a |
| Monosodium Phosphate | 5.00 | 0.16 | 0.16 | 0.16 | 0.16 | 0.16 | 0.16 | 0.16 | 0.16 | 0.16 |
| Sodium CMC | 0.05 | 0.05 | 0.05 | 0.05 | 0.05 | 0.05 | 0.05 | 0.05 | 0.05 | 0.05 |
| Methyl Salicuylate | 1.00 | 0.80 | 0.80 | 0.75 | 0.80 | 0.80 | 0.80 | 0.80 | 0.80 | 1.00 |
| Sodium Silicate | 4.00 | 3.00 | 3.00 | 3.75 | 3.00 | 3.50 | 3.50 | 4.00 | 5.00 | 4.00 |
| Flavor | 0.80 | 0.80 | 0.80 | 0.75 | 0.80 | 0.80 | 0.80 | 0.80 | 0.90 | 0.80 |
| Total | 100.00 | 100.00 | 100.00 | 100.00 | 100.00 | 100.00 | 100.00 | 100.00 | 100.00 | 100.00 |

TABLE 6

COMPARATIVE SAMPLES A-J: Prophy Pastes Formulations Having Unacceptable Handability/Splatter Rating

| Ingredient | Sample #A | Sample #B | Sample #C | Sample #D | Sample #E | Sample #F | Sample #G | Sample #H | Sample #I | Sample #J |
|---|---|---|---|---|---|---|---|---|---|---|
| Glycerin | 26.00 | 26.00 | 35.00 | 34.00 | 34.00 | 32.00 | 30.00 | 30.00 | 38.00 | 32.00 |
| Pumice FF | 29.95 | 28.99 | 28.65 | 30.25 | 30.25 | 32.05 | 27.45 | 32.25 | 32.75 | 34.00 |
| Pumice O | 8.00 | 8.00 | 5.00 | 10.00 | 10.00 | 10.00 | 10.00 | 5.00 | 0.00 | 0.00 |
| Sodium | n/a | n/a | n/a | 2.70 | 2.70 | 2.70 | n/a | 1.40 | n/a | 2.70 |

TABLE 6-continued

COMPARATIVE SAMPLES A-J: Prophy Pastes Formulations Having Unacceptable Handability/Splatter Rating

| Ingredient | Sample #A | Sample #B | Sample #C | Sample #D | Sample #E | Sample #F | Sample #G | Sample #H | Sample #I | Sample #J |
|---|---|---|---|---|---|---|---|---|---|---|
| Fluoride | | | | | | | | | | |
| Sodium MFP | 9.40 | 9.40 | 9.40 | n/a | n/a | n/a | 9.30 | 4.50 | 9.40 | 9.40 |
| Calcium Citrate | 10.00 | 10.00 | 10.00 | 10.00 | n/a | n/a | n/a | 2.0 | n/a | 10.00 |
| Calcium Malate | n/a | n/a | n/a | n/a | 10.00 | 10.00 | 10.00 | n/a | 10.00 | n/a |
| Calcium Citrate Malate | n/a | n/a | n/a | n/a | n/a | n/a | n/a | 8.00 | n/a | n/a |
| Sodium Phosphate Dibasic | n/a | n/a | n/a | n/a | n/a | n/a | n/a | 1.00 | n/a | 2.00 |
| Calcium Phosphate Tribasic | 1 | n/a | n/a | n/a | n/a | n/a | n/a | 3.00 | n/a | 3 n/a |
| Water | 12.20 | 12.20 | 8.20 | 8.40 | 8.40 | 8.40 | 8.40 | 7.00 | 3.00 | 5.55 |
| Sodium Saccharin | 0.04 | n/a | 0.04 | 0.04 | 0.04 | 0.04 | 0.04 | 0.04 | 0.04 | 0.04 |
| Xylitol | n/a | 1.00 | n/a | n/a | n/a | n/a | n/a | n/a | n/a | n/a |
| Monosodium Phosphate | 0.16 | 0.16 | 0.16 | 0.16 | 0.16 | 0.16 | 0.16 | 0.16 | 0.16 | 0.16 |
| Sodium CMC | 0.05 | 0.05 | 0.05 | 0.05 | 0.05 | 0.05 | 0.05 | 0.05 | 0.05 | 0.05 |
| Methyl Salicuylate | 0.80 | 0.80 | 0.80 | 0.80 | 0.80 | 0.80 | 0.80 | 0.80 | 0.80 | 1.00 |
| Sodium Silicate | 2.60 | 2.60 | 1.90 | 2.80 | 2.80 | 3.00 | 3.00 | 4.00 | 5.00 | 5.00 |
| Flavor | 0.80 | 0.80 | 0.80 | 0.75 | 0.80 | 0.80 | 0.80 | 0.80 | 0.90 | 0.80 |
| Total | 100.00 | 100.00 | 100.00 | 100.00 | 100.00 | 100.00 | 100.00 | 100.00 | 100.00 | 100.00 |

TABLE 7

| SAMPLE No. | HANDABILITY OBSERVATIONS | ESTIMATED HANDABILITY RATING |
|---|---|---|
| SAMPLE #5 | Mixes easily, Self levels upon filling, cures within 12-24 hrs DPA Loads 100% after 3rd plunge, no excessive paste on exterior of non-latex applicator cup after 10 consecutive plunges. No splatter observed | 2 |
| SAMPLE #6 | Mixes easily, Self levels upon filling, cures within 12-24 hrs DPA Loads 100% after 3$^{rd}$ plunge, no excessive paste on exterior of non-latex applicator cup after 10 consecutive plunges. No splatter observed. | 1 |
| SAMPLE #7 | Mixes easily, Self levels upon filling, cures within 12-24 hrs DPA Loads 100% after 4th plunge, very slight excessive paste on exterior of non-latex applicator cup after 10 consecutive plunges. No splatter observed. | 2 |
| SAMPLE #8 | Mixes easily, Self levels upon curing, Cures within 12-24 hrs. DPA Loads 100% after 4$^{th}$ plunge, no excessive paste on exterior of non-latex applicator cup after 10 consecutive plunges. No splatter observed. | 3 |
| SAMPLE #9 | Mixes easily, Self levels upon filling cures within 12-24 hrs DPA Loads 100% after 3$^{rd}$ plunge, no excessive paste on exterior of non-latex applicator cup after 10 consecutive plunges. No splatter observed. | 2 |
| SAMPLE #10 | Mixes easily, Self levels upon filling cures within 12-24 hrs DPA Loads 100% first plunge, no excessive paste on exterior of non-latex applicator cup after 10 consecutive plunges. No splatter observed | 3 |
| SAMPLE #11 | Mixes easily, Self levels upon filling cures within 12-24 hrs DPA Loads 100% after 3$^{rd}$ plunge, no excessive paste on exterior of non-latex applicator cup after 10 consecutive plunges. No splatter observed. | 2 |
| SAMPLE #12 | Mixes easily, Self levels upon filling cures within 12-24 hrs DPA Loads 100% after 4th plunge, very slight excessive paste on exterior of non-latex applicator cup after 10 consecutive plunges. No splatter observed. | 2 |
| SAMPLE #14 | Mixes easily, Self levels upon filling cures within 12-24 hrs DPA Loads 100% after 3$^{rd}$ plunge, no excessive paste on exterior of non-latex applicator cup after 10 consecutive plunges. No splatter observed. | 2 |
| SAMPLE #15 | Mixes easily, Self levels upon filling cures within 12-24 hrs DPA Loads 100% after 4th plunge, no excessive paste on | |

TABLE 7-continued

| SAMPLE No. | HANDABILITY OBSERVATIONS | ESTIMATED HANDABILITY RATING |
|---|---|---|
| | exterior of non-latex applicator cup after 10 consecutive plunges. No splatter observed. | |
| COMPARATIVE SAMPLE # A | Mixes easily, too fluid, cures within 36-48 hrs. Tacky after curing. DPA Loads 100% after $2^{nd}$ plunge, excessive paste on exterior of non-latex applicator cup after 10 consecutive plunges. Slight splatter observed. | 4 |
| COMPARATIVE SAMPLE # B | Mixes easily, too fluid, cures within 36-48 hrs. Tacky after curing. DPA Loads 100% after 2nd plunge, excessive paste on exterior of non-latex applicator cup after 8 consecutive plunges. Excessive splatter observed | 8 |
| COMPARATIVE SAMPLE # C | Mixes easily, too fluid, cures within >48 hrs. Soft and tacky after curing. DPA Loads 100% after $3^{rd}$ plunge, excessive paste on exterior of non-latex applicator cup after 5th consecutive plunge Excessive splatter observed | 8 |
| COMPARATIVE SAMPLE # D | Mixes easily, too fluid, cures within 24-36 hrs. Tacky after curing. DPA Loads 100% after $3^{rd}$ plunge, no excessive paste on exterior of non-latex applicator cup after 10 consecutive plunges Slight to moderate splatter observed | 4 |
| COMPARATIVE SAMPLE # E | Mixes easily, Self levels, cures within 24-36 hrs. Tacky after curing. DPA Loads 100% after $1^{st}$ plunge, excessive paste on exterior of non-latex applicator cup after $2^{nd}$ consecutive plunge Excessive splatter observed | 8 |
| COMPARATIVE SAMPLE # F | Mixes easily. Self levels with vibration, cures within 24 hrs. Slight liquid separation was noted after 72 hrs. DPA Loads 100% after $2nd^{t}$ plunge, excessive paste on exterior of non-latex applicator cup after $3^{rd}$ consecutive plunge Excessive splatter observed | 8 |
| COMPARATIVE SAMPLE # G | Mixes easily. Self levels with vibration cures within 12-24 hrs. Slight liquid separation was noted after 72 hrs. DPA Loads 100% after $1^{st}$ plunge, excessive paste on exterior of non-latex applicator cup after $2^{nd}$ consecutive plunge Excessive splatter observed | 10 |
| COMPARATIVE SAMPLE # H | Mixes easily. Self levels with vibration cures within 12-24 hrs Paste is slightly stiff. DPA Loads 100% after 4th plunge, excessive paste on exterior of non-latex applicator cup after $8^{th}$ consecutive plunge. Moderate splatter observed | 6 |
| COMPARATIVE SAMPLE # I | Mixes easily, too fluid, cures within 24-36 hrs. Tacky after curing. DPA Loads 100% after 7th plunge, excessive paste on exterior of non-latex applicator cup after 10 consecutive plunges Slight to moderate splatter observed | 4 |
| COMPARATIVE SAMPLE # J | Mixes easily, too fluid, cures within 12-24 hrs. Stiff and Tacky after curing. DPA Loads 100% after 7th plunge, excessive paste on exterior of non-latex applicator cup after 7 consecutive plunges. Moderate splatter observed. | 6 |

As a result of the comparison of Table 5 and Table 6 and observations noted in Table 7, a major influence to the handability and splatter characteristics is the relationship of water to remineralizing agents (e.g., Calcium, Phosphate and Fluoride). The Inventive Examples #5 thru #12 have a ratio range of water to remineralizing agents (Ca, P, F) of about 0.1 to 0.3:1 and the Comparative Examples #16 thru #22 have a ratio range of about 0.4 to 0.6:1.

Examples #5 and #6 have water to remin (Ca, P, F) ratio of about 0.1:1, a silicate matrix to remin ratio of about 0.28:1 (#5) and 0.18:1 (#6) respectively, a silicate matrix ratio of silicate to methyl salicylate of 4:1 (#5) and 3.75:1 (#6). Both formulations exhibit a handability/splatter rating of less than or equal to 2.

Example #5 and Comparative Example #19 and #20 have water to remin ratio of about 0.1:1 (#5) and 0.66:1 (#19, #20) respectively, a silicate matrix to remin ratio of 0.28:1, a silicate matrix ratio of silicate to methyl salicylate of 4:1 (#5), 3.5:1 (#19, #20) respectively. Example #5 has a Handability/Splatter Rating of 2, Comparative Example #19 is 4, and #20 is 8.

Examples #6 and #8 have a water to remin ratios of 0.1:1 (#6) and 0.22:1(#8) respectfully, a curing system to remin ratio of about 0.18:1 and 0.23:1 respectfully, a silicate matrix ratio of silicate to methyl salicylate of 3.75:1 (#6) and 5:1 (#8). Both formulations exhibit a handability/splatter rating of less than or equal to 2.

Examples #6 and #11 Have a water to remin ratio of about 0.1:1, a silicate matrix to remin ratio of about 0.18:1 (#6) and 0.21:1 (#11) respectfully, a silicate matrix ratio of silicate to methyl salicylate of 3.7:1 (#6) and 4.4:1. (#11.) Both formulations exhibit a handability/splatter rating of less than or equal to 2.

Examples #7 and #9 have water to remin ratio of about 0.1:1, a silicate matrix to remin ratio of about 0.24:1 (#7) and 0.18:1(#9) respectively, similar silicate matrix ratio of silicate to methyl salicylate of 3.75. Both formulations exhibit handability/splatter rating of 2.

Examples #8 and #12 have water to remin ratios of about 0.22:1 (#8) and 0.15:1 (#12) respectively, a silicate matrix to remin ratio of about 0.2:1, a silicate matrix ratio of silicate to methyl salicylate of 5:1. Both formulations exhibit a handability/splatter rating of 2.

Example #8 and Comparative Example #18 have water to remin ratio of about 0.22:1 (#8) and 0.42:1 (#18) respectively, a silicate matrix to remin ratios of 0.23:1 (#8) and 0.14:1 (#18) respectively, a silicate matrix ratio of silicate to methyl salicylate of 5:1 (#8) and 2.4:1 (#18) respectively. Example #8 has a Handability/Splatter Rating of 2 and Comparative Example #18 is 8.

Example #9, #10, #11 and Comparative Example #22 have water to remin ratio of about 0.1:1 (#9, #10, #11) and 0.44:1 (#22) respectively, a silicate matrix to remin ratio 0.18:1 (#9) and 0.2:1 (#22) respectively, a silicate matrix ratio of silicate to methyl salicylate of 3.75:1 (#9, #18) respectively. Example #9 has a Handability/Splatter Rating of 2 and Comparative Example #22 is 10.

Example #9, #10, #11 and Comparative Example #22 have water to remin ratio of about 0.1:1 (#9, #10, #11) and 0.44:1 (#22) respectively, a silicate matrix to remin ratio 0.18:1 (#9) and 0.2:1 (#10, #11, #22) respectively, a silicate matrix ratio of silicate to salicylate of 3.75:1 (#9, #22) and 4.3:1 (#10, #11) respectively. Example #9, ·10, #11 have a Handability/ Splatter Rating of less than or equal to 3 and Comparative Example #22 is 10.

Example #12 and Comparative Example #23 have a water to remin ratio of 0.15:1 (#12) and 0.39:1 (#23) respectfully, a silicate matrix to remin ratio of 0.23:1 (#12) and 0.27:1 (#23) respectfully, a silicate matrix ratio of silicate to methy salicylate of 5:1 (#12, #23). Example #12 has a Handability/ Splatter Rating of 2 and Comparative Example #23 is 6.

Comparative Examples #17 and #21 have water to remin ratios of about 0.6:1, a silicate matrix to remin ratio of 0.17:1 (#17) and 0.29:1 (#21) respectively, a similar silicate matrix ratio of silicate to methyl salicylate of 3:1. Both formulations exhibit handability/splatter rating of 8.

Comparative Examples #18 and #19 have water to remin ratio of about 0.42:1 (#18) and 0.66:1 (#19) respectively, a silicate matrix to remin ratio of 0.14:1 (#18) and 0.28:1 (#19) respectively, a silicate matrix ratio of silicate to methyl salicylate of 2.4:1 (#18) and 3.2:1 (#19) respectively. Comparative Example 18 formulation exhibits a handability/splatter rating of 8 and Example 19 is 4.

Comparative Examples #18 and #22 have water to remin ratio of about 0.4:1, a silicate matrix to remin ratio of 0.14:1 (#18) and 0.19:1 (#22) respectively, a silicate matrix ratio of silicate to methyl salicylate of 2.4:1 (#18) and 3.7:1 (#22) respectively. Both formulations exhibit a handability/splatter rating of 8-10.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A dental prophylactic paste comprising:
    from about 2 to 12 weight percent of at least one water soluble calcium salt;
    from about 2 to 12 weight percent of at least one water soluble phosphate salt;
    a silicate matrix comprising a water soluble silicate and one or more of an acid forming agent or a salicylate, wherein the silicate matrix is present in the paste from about 2 to 6 weight percent; and
    from about 10 to 60 weight percent of a moisture retention agent; and
    from about 1 to 8 weight percent of water, and wherein the paste has a splatter rating of less than 3.

2. The paste of claim 1, wherein the water soluble silicate is present in an amount that is from about 2 to 10 weight percent and is selected from lithium silicate, sodium silicate, potassium silicate and ammonium silicate, and mixtures thereof.

3. The paste of claim 1, wherein the silicate matrix comprises methyl salicylate and sodium silicate.

4. The paste of claim 1, further comprising sodium carboxymethyl cellulose.

5. The paste of claim 1, wherein the moisture retention agent is glycerin.

6. The paste according to claim 1, further comprising a fluoride containing compound that is present in an amount from about 0.02 to 12 weight percent, based on the total weight of the paste.

7. The paste according to claim 1, wherein the silicate matrix and a total amount of the calcium and phosphate salts in the paste are present in a ratio of about 0.3:1.

8. The paste according to claim 1, wherein the moisture retention agent and a total amount of the calcium and phosphate salts in the paste are present in a ratio about 3:1.

9. The paste according to claim 1, wherein the water and a total amount of the calcium and phosphate salts in the paste are present in a ratio about 0.2:1.

10. The paste of claim 1, further comprising an abrasive agent selected from the group consisting of amorphous aluminum silicate, also commonly known as pumice, fused sodium potassium aluminum silicate, also commonly known as perilite, diatomaceous earth, and combinations thereof.

11. The paste of claim 10, wherein the amount of abrasive agent is from about 24 to 48 weight percent.

12. The paste of claim 11, wherein the ratio of abrasive agent to the total amount of calcium and phosphate salts is from about 3:1.

13. The paste of claim 1, further comprising a desensitizing agent selected from the group consisting of potassium bicarbonate, potassium citrate, potassium chloride, potassium nitrate, strontium chloride, strontium acetate, strontium nitrate, or mixtures thereof.

14. A dental prophylactic paste having low splattering and remineralization properties comprising from about 3 to 6 weight percent of a phosphate salt, from about 2 to 12 weight percent of a calcium salt; from about 0.02 to 12 weight percent of a fluoride containing compound, from about 2 to 6 weight percent of a combination of an alkali silicate and a salicylate, from about 0.02 to 0.5 weight percent of sodium carboxymethyl cellulose, from about 36 to 42 weight percent glycerin, from about 2 to 6 percent water, and from about 24 to 48 weight percent of an abrasive agent, and wherein the percent weight ratio of glycerin to the total amount of calcium and phosphate salts and fluoride containing compound is from about 1.5 to 3:1.

15. The dental paste of claim 14, wherein the paste has a Splatter Rating of less than 3.

16. The dental paste of claim 14, wherein the paste has a Splatter Rating of less than 2.

17. The dental paste of claim 14, wherein an SEM image of a dentin disk having open dental canaliculi prior to treatment with the paste shows that substantially all of the open dental canaliculi in the area of the dentin disk treated with the paste have been remineralized.

18. The paste according to claim 14, wherein a combination of the sodium silicate and methyl salicylate and a total amount of the calcium and phosphate salts and fluoride containing compound in the paste are present in a ratio from about 0.25:1 to 0.75:1.

19. The paste according to claim 14, wherein the water and a total amount of the calcium and phosphate salts and fluoride containing compound in the paste are present in a ratio from about 0.1:1 to 0.3:1.

20. The paste of claim 19, wherein the amount of abrasive agent is from about 28 to 42 weight percent.

21. The paste of claim 14, wherein the ratio of abrasive agent to the total amount of calcium and phosphate salts and fluoride is from about 1.5 to 3:1.

22. A method of treating a patient's teeth comprising the steps of applying the paste of claim 1 to a patient's teeth using a rotating instrument having an applicator tip with a cup or brush.

* * * * *

UNITED STATES PATENT AND TRADEMARK OFFICE
CERTIFICATE OF CORRECTION

| | |
|---|---|
| PATENT NO. | : 8,741,268 B2 |
| APPLICATION NO. | : 12/556913 |
| DATED | : June 3, 2014 |
| INVENTOR(S) | : Peterson |

It is certified that error appears in the above-identified patent and that said Letters Patent is hereby corrected as shown below:

In the claims:

Column 18,
Line 38, "from about 3:1." should read --about 3:1.--;
Line 50, "0.5" should read --.5--.

Page 1 of 1

Signed and Sealed this
Thirtieth Day of September, 2014

Michelle K. Lee
*Deputy Director of the United States Patent and Trademark Office*